United States Patent [19]
Child et al.

[11] Patent Number: 5,345,027
[45] Date of Patent: Sep. 6, 1994

[54] ALKYLATION PROCESS USING CO-CURRENT DOWNFLOW REACTOR WITH A CONTINUOUS HYDROCARBON PHASE

[75] Inventors: Jonathan E. Child, Sewell; Kenneth J. Del Rossi, Woodbury, both of N.J.; Albin Huss, Jr., Chadds Ford, Pa.; Frederick J. Krambeck, Cherry Hill; Thomas R. Melli, Sewell, both of N.J.; Sergei Yurchak, Media, Pa.

[73] Assignee: Mobile Oil Corp., Fairfax, Va.

[21] Appl. No.: 933,163

[22] Filed: Aug. 21, 1992

[51] Int. Cl.$^5$ .......................... C07C 2/56; C07C 2/58
[52] U.S. Cl. .................................. 585/720; 585/709; 585/721; 585/726
[58] Field of Search ............... 585/709, 720, 721, 726

[56] References Cited

U.S. PATENT DOCUMENTS

| | | |
|---|---|---|
| 2,363,222 | 11/1944 | Beyerstedt . |
| 2,401,844 | 6/1946 | Schulze et al. . |
| 2,404,599 | 7/1946 | Sanderson ........................ 585/720 |
| 2,437,544 | 3/1948 | Marisic ............................. 585/720 |
| 3,088,987 | 5/1963 | Irvine ............................... 585/720 |
| 3,155,742 | 11/1964 | Holzman .......................... 585/720 |
| 3,179,712 | 4/1965 | Carson ............................. 585/720 |
| 3,873,634 | 3/1975 | Hoffman . |
| 3,976,713 | 8/1976 | Holmes et al. . |
| 4,385,985 | 5/1983 | Gross et al. ..................... 208/113 |
| 4,797,262 | 1/1989 | Dewitz .............................. 422/142 |

Primary Examiner—Patrick P. Garvin
Assistant Examiner—E. D. Irzinski
Attorney, Agent, or Firm—Alexander J. McKillop; Malcolm D. Keen; Dennis P. Santini

[57] ABSTRACT

A continuous alkylation process for the production of high octane gasoline comprising contacting a mixture of an isoparaffin and an olefin with a catalyst complex comprising $BF_3:H_3PO_4$ in a continuous hydrocarbon downflow reactor.

13 Claims, 1 Drawing Sheet

ALKYLATION PROCESS USING CO-CURRENT DOWNFLOW REACTOR WITH A CONTINUOUS HYDROCARBON PHASE

FIELD OF THE INVENTION

The present invention relates to a novel alkylation process employing $BF_3$ promoted phosphoric acid as the catalyst complex whereby the catalyst is dispersed into a continuous hydrocarbon phase in a downflow reaction vessel.

BACKGROUND OF THE INVENTION

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so called alkylate. This alkylate is a valuable blending component in the manufacture of gasolines due not only to its high octane rating but also to its ability to meet the compositional requirements of reformulated gasolines.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive than the sulfuric process and is more easily recovered and purified.

Both hydrofluoric and sulfuric catalysts are gradually depleted in continuous alkylation processes and must be regenerated or replenished by mixture with fresh acid to maintain acid strength, reaction rate, and the resulting alkylate quality. Specifically, alkylate quality responds directly to increasing acid strength, and the acid makeup or regeneration rate is typically controlled together with other process variables such as temperature and space velocity, to meet a required alkylate quality specification. Both sulfuric acid and hydrofluoric acid alkylation share inherent drawbacks including environmental and safety concerns, acid consumption and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397 (1988). For a survey of hydrofluoric acid catalyzed alkylation, see 1 *Handbook of Petroleum Refining Processes* 23–28 (R. A. Meyers, Ed. 1986). Catalyst complexes comprising $BF_3$ as well as $BF_3$: $H_3PO_4$ adducts have been proposed by co-pending and co-assigned U.S. applications Ser. Nos. 608,783, 790,324 and 608,856. These applications are herein incorporated by reference. In co-pending application Ser. No. 608,783 a catalyst complex comprising the reaction product of $BF_3$ and $H_3PO_4$ was used in molar ratios of 0.5:1 to about 1.5:1 with the addition of excess $BF_3$ in concentrations of about 10 ppm to about 5% by weight of the total feed stock. In co-pending application Ser. No. 608,763, a catalyst complex comprising $BF_3$: $H_3PO_4$ adduct and at least one polar hydrocarbon formed in situ was used to avoid alkylation byproducts and improve isoparaffin: olefin alkylation selectivity. In co-pending application Ser. No. 790,324 alkylation is accomplished using a catalyst complex comprising a Lewis acid and at least one material selected from the group consisting of a protic solvent having a pKa less than about 16, a zeolitic or nonzeolitic solid and an ion exchange resin. The reaction takes place under alkylation conditions including temperatures from about $-40°$ to about $500°$ C., and pressure from subatmospheric to about 5000 psig.

U.S. Pat. No. 2,345,095 to Bruner teaches a paraffin-olefin alkylation process catalyzed by a boron tri-fluoride-water complex, represented by the formula $BF_3:nH_2O$, where n is preferably from 1 to 1.5. The Brunet reference notes on page 2 left hand column, lines 13–23, that the $BF_3:H_2O$ catalyst complex behaves similarly to sulfuric acid but is a superior alkylation catalyst because $BF_3:H_2O$ does not promote oxidation to undesired byproducts.

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product. The Slotterbeck '370 and '371 patents also discuss loss of catalytic activity due to diminishing acid strength; see the Slotterbeck '370 patent at page 2, right hand column at line 75 through page 3, left hand column at line 55 and the Slotterbeck '371 patent at page 2, right hand column at line 66, through page 3, left hand column at line 41. U.S. Pat. No. 3,873,634 to Hoffman teaches a method of increasing the rate of ethylene alkylation by isobutane by carrying out the reaction simultaneously with the alkylation of a small amount of a higher weight olefin in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to yield a liquid fuel.

The use of downflow reactors in petroleum processing has generally been for catalytic conversions using solid bed catalysts. For example, U.S. Pat. No. 4,797,262 to Dewitz discloses an integral hydrocarbon conversion catalytic cracking conversion apparatus for the catalytic conversion of hydrocarbons comprising a catalytic downflow reactor, an upflow catalytic riser regenerator and a cyclonic separator for separating out spent catalysts. The separator interconnects the exit of the downflow riser reactor with the inlet of the upflow riser regenerator by means of a pressure leg seal. Solid catalysts disclosed are aluminosilicates and metal oxides such as magnesium or zirconium. U.S. Pat. No. 3,976,713 to Holmes discloses an isoparaffin-olefin alkylation process using granular catalyst solids in a plurality of beds packed in series. The effluent of each bed is recycled to the inlet of said bed. The feed stream is fed downward through conventional distribution means through the solid bed catalysts. U.S. Pat. No. 2,363,222 to Beyerstadt relates to the use of boron trifluoride in phosphorous acids as a catalyst for the alkylation of isoparaffins with mono-olefins. This reference disclosed the preparation of a catalyst composition by bubbling boron trifluoride through the phosphorous acid and saturating the acid. This reference discloses that it is essential that the feed stock contain at least one paraffinic hydrocarbon containing at least one tertiary carbon atom per molecules and at least one olefin. The process may be carried out either as a batch or continuous process.

U.S. Pat. No. 4,385,985 discloses the use of a downflow riser in a fluid catalytic cracking process. The downflow riser is disclosed as affecting uniform distribution of the catalyst throughout the feed, decreasing the contact time of the catalyst with the feed and decreasing the amount of coke made in the process. The riser of the reaction vessel is placed on top of the reactor in such a manner that it forces the downflow movement of the regenerated catalyst mixed with the petroleum feedstock. Those catalyst disclosed are zeolites, silica-alumina and carbon monoxide burning promoters such as platinum metals e.g., platinum, palladium, rhodium, ruthenium, iridium and osmium. This process uses an apparatus which includes a riser mounted on a reaction vessel, a steam stripper section and a catalyst regenerator riser.

U.S. Pat. No. 2,401,884 to Schulz et al. discloses an alkylation process using liquid catalysts such as boron tri-fluoride which are pretreated with an olefin having a fewer number of carbon atoms per molecule than the olefin used as the principle alkylating reactant. An inorganic catalyst complex with boron tri-fluoride is prepared and pretreated with, for example, ethylene prior to contact with mixtures containing isoparaffins and higher olefins. This complex is said to be more stabilized and resistant to degradation than the catalysts would be without pretreatment.

Catalysts complexes comprising $BF_3$ as well as $BF_3:H_3PO_4$ adducts have overcome many of the safety and environmental draw backs of sulfuric and hydrofluoric acid alkylation systems. However, the volume and quality of alkylates using these catalysts has not always been comparable to that of sulfuric or hydrofluoric acid alkylates.

Traditional catalytic isoparaffin-olefin alkylation processes typically require excess isoparaffin and generally exhibit a direct relationship between increasing isoparaffin concentration and alkylate octane quality. The isoparaffin is an expensive feedstock and for this reason the isoparaffin is typically separated from the alkylate product stream and recycled to the alkylation reaction zone. The isoparaffin:olefin ratio for alkylation in the presence of certain $BF_3$-containing catalysts complexes must typically exceed about 5:1 to produce an alkylate of acceptable quality.

$BF_3:H_3PO_4$ catalyst complexes have a relatively high viscosity, making the use of standard upflow reactors typically used for HF alkylation somewhat impractical. Up until now, however, only upflow reactors have been used with these catalyst systems. This is because the continuous phase of standard alkylation processes is generally the acid phase. Due to the high viscosity of the acid phase in phosphoric promoted alkylation processes, a great deal of energy is required in stir reactors as well as other types of reactors which use upflow systems for generating alkylated product. The instant invention takes advantage of the inherent high viscosity and high density differences between the phosphoric acid phase and the hydrocarbon. As opposed to using the conventional continuous acid phase methods whereby hydrocarbon is dispersed in the acid medium to insure excess catalyst, the present invention uses the hydrocarbon as the continuous phase whereby the catalyst acid complex is disbursed into the top of the downflow reaction vessel. Thus, the invention provides a uniform dispersion of catalyst acid complex in a hydrocarbon continuous phase without the use of energy intensive stir reactors or the like. The result is a lower cost process with desirable octane yield and catalyst activity.

SUMMARY OF THE INVENTION

The present invention concerns an improved continuous alkylation process for producing high octane gasoline including contacting a mixture of an isoparaffin and an olefin with a catalyst complex comprising $BF_3:H_3PO_4$ in a hydrocarbon continuous downflow reactor. The discontinuous phase of acid catalyst is charged downwardly through a continuous phase of hydrocarbon reactants. This process overcomes the prior art problems associated with unstable acid catalyst complexes and increased catalyst viscosity which results in less effective circulation and heat transfer within the reaction mixture. Acids such as $H_2SO_4$ and HF have been known to work using conventional technology only when they are used as the dispersed medium, i.e., the hydrocarbon is dispersed into the acid medium. This results in excess acid. The present invention allows for elimination of HF and $H_2SO_4$ alkylation by using an alternative catalyst system which overcomes the traditional high viscosity problems associated with phosphoric acid.

DESCRIPTION OF THE DRAWING

The Figure is a simplified schematic diagram illustrating the major processing steps of the present invention.

DETAILED DESCRIPTION OF THE INVENTION

Figure 1:
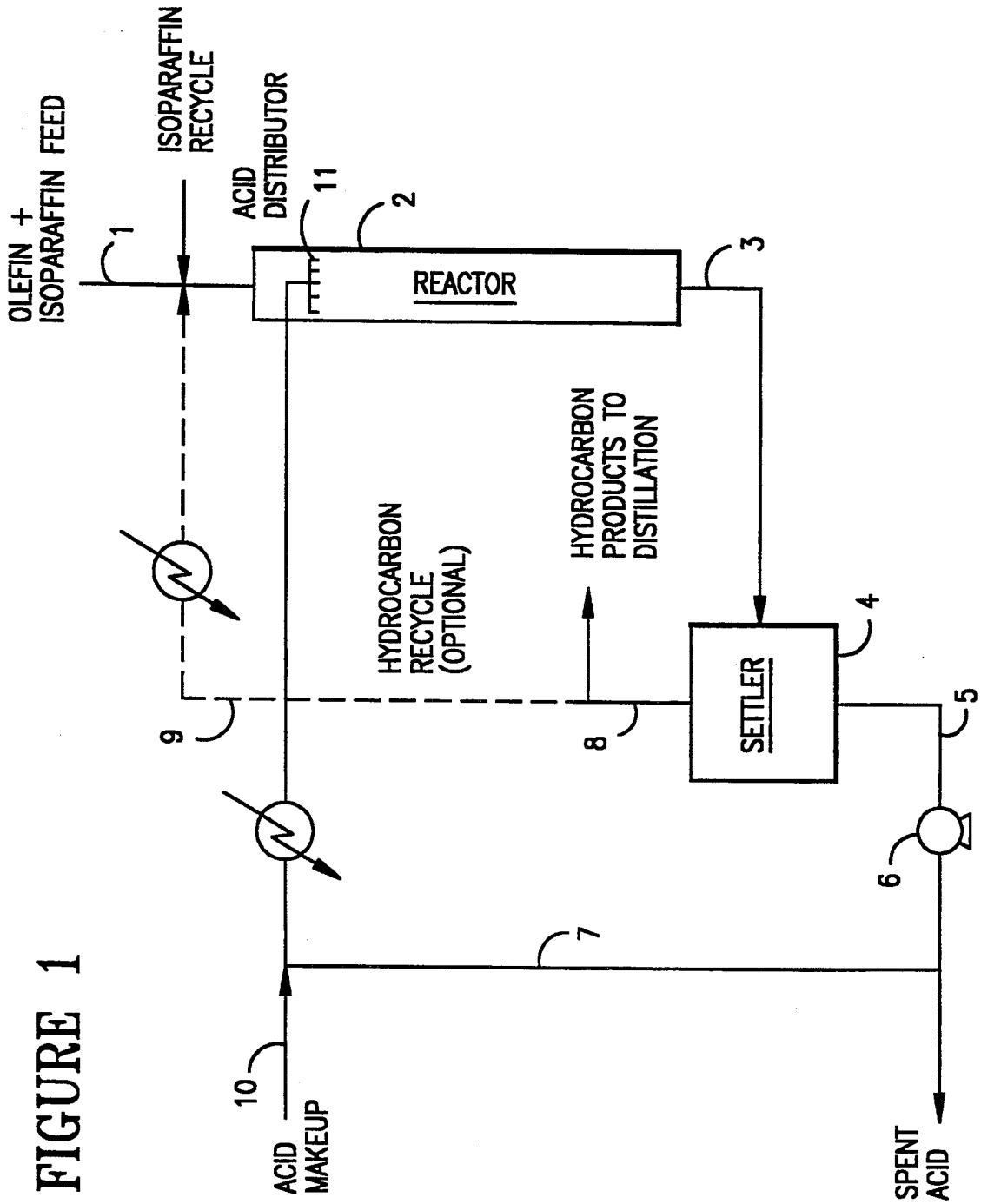

The process of the present invention converts a feedstock containing at least one isoparaffin having from 4 to 8 carbon atoms and at least one olefin having from 2 to 12 carbon atoms to a product stream containing a higher molecular weight isoparaffin. The present process further includes a means of producing alkylate product without expensive separating techniques which separate the dense alkylation catalyst from the less dense hydrocarbon phase.

More particularly, the present invention concerns an improved continuous alkylation process for producing high octane gasoline comprising contacting a mixture of an isoparaffin and an olefin with catalyst complex comprising $BF_3:H_3PO_4$ in a hydrocarbon continuous downflow reactor.

The result of using the present process is an increase in octane yield. Thus, another embodiment of the present invention is a method of increasing the octane yield in an alkylation process using $BF_3:H_3PO_4$ as a catalyst complex comprising maintaining the complex in a continuous co-current downstream hydrocarbon dispersion phase comprising isoparaffin and olefin.

Furthermore, catalyst acid viscosity is controlled during alkylation. Thus, additional embodiments of the present process include a method of increasing catalytic activity and stability of a $BF_3:H_3PO_4$ complex in an alkylation process comprising dispersing the complex in a continuous hydrocarbon co-current downflow reactor; and a method of controlling catalyst acid viscosity in isoparaffin/olefin alkylation where $BF_3:H_3PO_4$ is used as the acid catalyst complex said method comprising maintaining the catalyst complex dispersed substantially uniformly in the isoparaffin/olefin mixture in a continuous co-current downflow reactor.

FEEDSTOCKS

Feedstocks useful in the present alkylation process include at least one isoparaffin and at least one olefin. The isoparaffin reactant used in the present alkylation process has from 4 to 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, pentene, ethylene, hexene, octene and heptene, to name a few. The preferred olefins include the $C_4$ olefins, for example, butene-1, butene-2, isobutylene or a mixture of one or more of these. Butene-2 is the most preferred. Suitable feedstocks for the process of the present invention are described in U.S. Pat. No. 3,862,258 to Huang et al. at column 3, lines 44–56, the disclosure of which is herein incorporated by reference.

The weight ratio of isoparaffin to olefin in the total feed of the alkylation reaction zone is generally between 1.5:1 and 100:1 preferably between 5:1 and about 50:1. Suitable total fresh feedstocks contain isoparaffin and olefin in an isoparaffin:olefin weight ratio of from greater than about 1:1 up to about 10:1. The total feed to the alkylation reaction zone contains both fresh feed and recycled feed.

PROCESS CONDITIONS

The present alkylation process is suitably conducted at temperatures from about 0° F. (−18° C.) to about 200° F. (38° C.) and preferably about 30° F. (−1° C.) to about 60° F. (16° C.). Lower reaction temperatures are preferred to maximize alkylate octane.

Operating pressure is controlled to maintain the reactors in the liquid phase, and is suitably from about 50 to about 1500 psig, preferably from about 50 to about 500 psig and most preferably about 100 to about 200 psig.

The catalyst weight hourly space velocity (WHSV) as well as the acid dosage varies with the particular catalyst system employed. Hydrocarbon and catalyst flow through the alkylation zone is typically controlled to provide WHSV sufficient to convert about 99% by weight or greater of olefin feed to alkylate product. Typical WHSV values fall within the range from about 0.01 to about 10 hours$^{-1}$.

The particular operating conditions used in the present invention will depend to some degree on the specific alkylation reaction being effected. Process conditions such as temperature, pressure and space velocity as well as molar ratio of the reactants will affect the characteristics of the resulting alkylate and may be adjusted within the disclosed ranges by those skilled in the art through routine experimentation.

The present process is carried out in a downflow reactor as opposed to more conventional continuous stirred reactors such as those employed in sulfuric acid alkylation. While stirring reactors can be employed in the present invention, they are not preferred because of the large stirrers required to disperse the acid in the hydrocarbon phase. Pumps typically are more reliable and less expensive than large stirrers and are better suited for the present process.

CATALYST COMPLEX

The catalyst complex of the present invention comprises about 4 to about 65 weight percent $BF_3$, and from about 2 to about 60 weight percent $H_3PO_4$. Preferably, this complex comprises from about 24 to about 55 weight percent $BF_3$ and from about 23 to about 60 weight percent $H_3PO_4$. The ratio of catalyst complex to hydrocarbon is about 0.05:1 to about 0.8:1 by volume.

The alkylation reaction takes place at the interface between the reacting liquids and the catalyst. Various interface factors such as total available droplet surface area will therefore have a bearing on the reaction speed, efficiency and completeness. Additionally, the number and size of droplets will also have a bearing on the degree to which it is necessary to later separate out the droplets from the hydrocarbon phase. It is believed that a corelation exists between the amount and size of a catalyst droplet and the reaction time. For example, a given reaction time is believed to be directly proportional to the catalyst droplet size and inversely proportional to the amount of catalyst present. Thus, the size and number of catalyst droplets can be balanced to maximize the efficiency of the alkylation process.

As will be discussed further herein, different dispensing nozzles will yield a variety of droplet sizes, shapes and forms. Generally, the greater the pressure drop through the nozzle, the smaller the resulting droplet size. Nozzle size of course can be chosen for a particular application and these ranges are discussed further herein. The droplet size, however, is preferably within the range of about 200 to about 600 microns. Although in many instances it is preferred to have a relatively uniform droplet size, the same may be varied to achieve other intended results.

SOLUBILIZING AGENTS

The catalyst complex may optionally be added in conjunction with a solubilizing agent. For a general discussion of the characteristics of suitable solubilizing agents, see *Kirk-Othmer Encyclopedia of Chemical Technology*, 3rd ed., 332 (1982). Non-limiting examples of suitable solubilizing agents include sulfonic and phosphonic compounds, for instance, sulfated esters, sulfated alkanolamides, alkyl sulfates, sulfonates containing aliphatic, aromatic, alkylaromatic or naphthenic constituents, alkyl phosphates, alkyl polyphosphates, phosphate mono-esters, phosphate di-esters, and phosphate tri-esters.

PROCESS FLOW

The process of the present invention is suitably carried out in a downflow reactor. The feedstock is piped into the downflow reactor and travels downward under gravitational and internal pump pressure to the bottom of the reactor where it is withdrawn and piped into a settler tank where the more dense liquid alkylation catalyst rapidly migrates to the bottom and the gasoline product floats to the top. The liquid catalyst is then withdrawn from the settler and disposed or combined with fresh catalyst and sent back to the reactor. The gasoline product is collected from the top of the settler and either recycled back into the reactor vessel or sent to a distillation column where the product is fractionalized.

Referring now to FIG. 1, one embodiment of the present invention is schematically illustrated in which a continuous alkylation process is conducted in the presence of a discontinuous phase of acid catalyst complex comprising $BF_3:H_3PO_4$ in a downflow reaction vessel. The alkylation reaction of the present invention preferably proceeds under substantially anhydrous conditions, although water may optionally be present in the reaction zone at concentrations up to about 15 weight percent of the total catalyst complex.

The feedstock mixture of olefin and isoparaffin (isobutane) is added through line 1 into the top of downflow reactor 2 where it serves as the dispersion medium for the incoming acid catalyst. Acid catalyst is added from line 10 to the top of the reaction vessel 2 through acid distributor nozzles 11. The nozzles serve to disperse droplets of catalyst in the proper ratio into the reactor vessel where it is pulled downstream into the hydrocarbon phase and substantially uniformly distributed. The velocity of the catalyst through each nozzle can vary from about 20 to abut 500 feet per second and preferably about 50 to about 150 feet per second. In this instance the nozzle speed was in the latter range. The nozzle hole size can vary from 1/32" to about 2" and preferably to about ⅜ to ¾ of an inch. Commercial available nozzles are generally ⅜ of an inch in diameter. The nozzle hole size and acid velocity through the nozzle are maintained to produce acid droplets with diameters from about 0.005 cm to about 1 cm and preferably from about 0.01 cm. to about 0.1 cm. Smaller drops increase the rate of reaction but require more energy to make and are more difficult to separate from the hydrocarbon product. The reactants are continuously fed into the top of the reaction vessel and the reaction products are simultaneously continuously withdrawn from the bottom of reactor 2 through line 3 and deposited into settler tank 4 where the heavier acid catalyst complex settles to the bottom and is removed via line 5. The catalyst is then sent through pump 6 where acid which is now degenerated and no longer useful is sent to a waste disposal tank (not shown). Acid which remains still useful is recycled through line 7 where it is combined in line 10 with new incoming acid, the mixture of which is in turn fed into the reactor.

The total acid recycle makeup and the acid addition rate is controlled to maintain the concentration of the $BF_3$ in the catalyst complex from about 30 to about 65 weight percent based on the total weight of the catalyst complex present in the reaction zone.

The relative flow rates of isoparaffin and olefin are controlled to maintain an isoparaffin:olefin ratio of about 2:1 to about 50:1 and preferably about 3:1 to about 15:1 in the overall feed to the downflow reactor. The alkylate hydrocarbon product is lighter in density than the catalyst and floats to the top of the settler tank 4 where it is removed through line 8 and either sent to a distillation column (not shown) where it is fractionalized, or alternatively sent via line 9 to be recycled and combined with the incoming feedstock material.

EXAMPLE 1

To demonstrate the ability to run the alkylation reaction by dispersing the catalyst complex in a continuous phase, a feedstock comprising a 10:1 ratio of isobutane/2-butene was fed into a stirred tank reaction vessel. A complex of $BF_3:H_3PO_4$ complex was added at the top of the reaction vessel. The ratio of acid to oil was 0.1. The reaction was carried out in a continuous stirred autoclave at 50° F. and 150 psig and 1000 rpm stirring. A downflow reaction vessel is expected to yield similar results with increased efficiency. Table 1 shows a comparison between conventional sulfuric acid catalyzed alkylation and the present catalyst system under continuous hydrocarbon conditions. The sulfuric acid catalyzed alkylation could not be run using a continuous hydrocarbon phase, but rather requires a conventional continuous acid phase.

As can be seen from the table, the percent olefin conversion as well as the yield is higher in the $B_3:H_3PO_4$ catalyst then the sulfuric acid catalyst. Additionally, nearly twice as much $C_8$ product was obtained using the inventive process than sulfuric acid as evidenced from the table. A higher trimethylpentane/dimethylhexane (TMP/DMH) ratio, which is preferred, was also obtained using the catalyst of the inventive process.

Table 2 indicates the physical properties of various acid alkylation catalysts. It should be noted that the viscosity of the catalyst used in the inventive process is significantly higher than those of prior art catalysts. This fact is critical to the advantages and benefits of the instant invention since the process of using a downflow continuous hydrocarbon phase is designed to minimize the energy that would be required in circulating a uniform dispersion of a catalyst and hydrocarbon by dispersing the catalyst into the hydrocarbon phase. Additionally, not only is this process more efficient from an energy standpoint, it translates into a direct cost savings from a commercial point of view.

TABLE $BF_3:H_3PO_4$ vs. $H_2SO_4$ Under Hydrocarbon Continuous Conditions
Feed: 10/1 Isobutane/2-butene
Conditions: Acid/Oil Ratio 0.1, 50° F., 150 psig, 1000 rpm

| Catalyst | $BF_3:H_3PO_4$ | $BF_3:H_3PO_4$ | $H_2SO_4$ | $H_2SO_4$ |
| --- | --- | --- | --- | --- |
| Hours On-Stream | 151 | 248 | 4 | 6 |
| WHSV Based on Olefin, $hr^{-1}$ | 0.39 | 0.36 | 0.50 | 0.50 |
| $BF_3$ Rate, wt % of feed | 0.48 | 0.52 | — | — |
| Olefin Conversion, % | 100.0 | 100.0 | 98.8 | 98.6 |
| Yield (Grams $C_5$ + Product/Gram Olefin Converted) | 2.08 | 1.98 | 1.40 | 0.9 |
| Product Dist. in $C_5$ +, wt % | | | | |
| $C_5$–$C_7$ | 10.9 | 9.3 | 18.2 | 20.1 |
| $C_8$'s | 82.9 | 86.2 | 48.6 | 43.5 |
| $C_9$ + | 6.2 | 5.5 | 33.2 | 36.4 |
| TMP/DMH Ratio | 4.0 | 4.1 | 3.6 | 3.8 |
| R + M/2 | 94.7 | 95.1 | — | — |

TABLE 2

Physical Properties of Acid Alkylation Catalysts

| Acid | Density g/cc | Viscosity, CRT, cps | Boiling (or Decomposition) Temperature, °F. |
| --- | --- | --- | --- |
| HF | 0.99 | 0.48 | 67 |
| $H_2SO_4$ | 1.84 | 25.5 | 640 |
| $BF_3:H_3PO_4$ | 1.88 | 57.5 | >200 |
| Spent $BF_3:H_3PO_4$ (34 DOS) | — | 87.5 | — |

We claim:

1. A continuous alkylation process for alkylating an isoparaffin with an olefin under alkylation conditions in a downflow reactor comprising uniformly dispersing downwardly a catalyst complex comprising $BF_3:H_3PO_4$ into a continuous hydrocarbon phase comprising a mixture of said isoparaffin and said olefin.

2. A process of claim 1 wherein the isoparaffin contains from 4 to 8 carbon atoms and the olefin contains from 2 to 12 carbon atoms.

3. The process of claim 1 wherein the alkylation reaction temperature is from about 0° F. to about 200° F.

4. The process of claim 1 wherein the alkylation reaction pressure is in the range of about 50 to about 500 psig.

5. The process of claim 1 wherein the catalyst complex is uniformly dispersed from a nozzle distributor.

6. The process of claim 1 wherein the acid is dispersed as droplets with diameters from about 0.01 cm to about 0.1 cm.

7. A method of increasing catalytic activity and stability of a $BF:H_3PO_4$ complex in an alkylation process under alkylation conditions comprising dispersing the complex downwardly in a continuous hydrocarbon co-current downflow reactor.

8. The method of claim 7 wherein the alkylation process has a reaction temperature of about 0° F. to about 200° F.

9. The method of claim 8 wherein the alkylation process has a pressure range of from about 50 to about 100 psig.

10. The method of claim 7 wherein the ratio of $BF_3:H_3PO_4$ to hydrocarbon is about 0.05:1 to about 0.8:1.

11. A method of increasing the octane yield in an alkylation process under alkylation conditions using $BF_3:H_3PO_4$ as a catalyst complex comprising:
    dispersing the complex downwardly into a continuous hydrocarbon phase and,
    maintaining the complex in a continuous co-current downstream hydrocarbon phase comprising isoparaffin and olefin.

12. The method of claim 11 wherein the ratio of $BF_3:H_3PO_4$ to the continuous hydrocarbon phase is from about 0.08:1 to about 0.5:1.

13. A method of controlling catalyst acid viscosity in an isoparaffin/olefin alkylation process under alkylation conditions where $BF_3:H_3PO_4$ is used as the acid catalyst complex said method comprising:
    dispersing the complex downwardly into a continuous isoparaffin/olefin hydrocarbon phase and,
    maintaining the catalyst complex dispersed substantially uniformly in the isoparaffin/olefin phase in a continuous co-current downflow reactor.

* * * * *

UNITED STATES PATENT AND TRADEMARK OFFICE
CERTIFICATE OF CORRECTION

PATENT NO. : 5,345,027
DATED : September 6, 1994
INVENTOR(S) : Jonathan E. Child et al.

It is certified that error appears in the above-indentified patent and that said Letters Patent is hereby corrected as shown below:

Col. 9, line 15, Claim 7, "BF" should read --$BF_3$--.

Signed and Sealed this

Twenty-second Day of November, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,345,027
DATED : September 6, 1994
INVENTOR(S) : J.E. Child et al.

It is certified that error appears in the above-indentified patent and that said Letters Patent is hereby corrected as shown below: On the title page: Item

[73] Assignee "Mobile Oil Corp.," should be --Mobil Oil Corp.--

Signed and Sealed this

Sixth Day of June, 1995

Attest:

BRUCE LEHMAN

Attesting Officer

Commissioner of Patents and Trademarks